United States Patent [19]

Bortinger et al.

[11] Patent Number: 4,804,800

[45] Date of Patent: Feb. 14, 1989

[54] PROCESS FOR SYNTHESIZING A ZEOLITE CATALYST ON A PH CONTROLLED BASIS TO IMPROVE CATALYST LIFE

[75] Inventors: Arie Bortinger, Ridgewood; Robert A. Maggio, Long Valley; Wim J. M. Pieters, Morristown, all of N.J.

[73] Assignee: Exxon Research & Engineering Co., Florham Park, N.J.

[21] Appl. No.: 121,017

[22] Filed: Nov. 16, 1987

Related U.S. Application Data

[62] Division of Ser. No. 685,153, Dec. 21, 1984, abandoned.

[51] Int. Cl.$^4$ ................................................ C07C 1/00
[52] U.S. Cl. ....................................... 585/640; 585/733
[58] Field of Search ........................................... 585/640

[56] References Cited

U.S. PATENT DOCUMENTS

| | | | |
|---|---|---|---|
| 3,894,107 | 7/1975 | Butter et al. | 585/640 |
| 4,665,268 | 5/1987 | Lee et al. | 585/640 |
| 4,665,269 | 5/1987 | Chu et al. | 585/640 |
| 4,709,114 | 11/1987 | Rudewald et al. | 585/640 |

FOREIGN PATENT DOCUMENTS 0021674  1/1981  European Pat. Off. ............ 423/329

*Primary Examiner*—Curtis R. Davis
*Attorney, Agent, or Firm*—S. H. Markowitz; T. B. Morris

[57] ABSTRACT

A process for preparing a zeolite, e.g. ZSM-5, under controlled conditions of initial pH adjustment with an acid, $SiO_2/Al_2O_3$ mole ratio, and in the presence of sodium cations, is disclosed, as well as a process for using the same to synthesize olefins from methanol and/or dimethyl ether.

10 Claims, No Drawings

PROCESS FOR SYNTHESIZING A ZEOLITE CATALYST ON A PH CONTROLLED BASIS TO IMPROVE CATALYST LIFE

This is a division of Application Ser. No. 685,153, filed 12/21/84, abandoned.

BACKGROUND OF THE INVENTION

This invention relates to methods of preparing shape selective zeolite catalysts, such as ZSM-5, and methods for their use to synthesize hydrocarbons such as olefins, in particular by conversion of lower monohydric alcohols and/or their ether derivatives.

Olefins, especially ethylene and propylene, are used on a large scale as intermediates for the manufacture of staple products such as olefin polymers, ethylene oxide, non-ionic detergents, glycols and fibre-forming polyesters. Processes for producing olefins usually involve non-catalytic pyrolysis of volatile hydrocarbons such as natural gas liquids or petroleum distillates. Catalytic pyrolysis processes have been proposed but do not appear to have reached industrial use.

In countries where such volatile hydrocarbons are not accessible but such feedstocks as coal, oil shale and methane, and consequently carbon monoxide/hydrogen synthesis gas derived therefrom, are available, it would be desirable to produce olefins from synthesis gas. It has been proposed to do this by converting the synthesis gas to methanol or to hydrocarbons and/or their oxygenated derivatives and reacting such products over shape selective acidic zeolites, e.g., of the ZSM-5 family. (See for example U.S. Pat. Nos. 3,894,106; 3,894,107; 4,025,571; and 4,052,479).

Shape selective zeolite materials, both natural and synthetic, have been demonstrated in the past to have catalytic capabilities for various types of organic compound conversions. These materials are ordered porous crystalline metalosilicates (e.g. aluminosilicates) having a definite crystalline structure within which there are a large number of cavities and channels, which are precisely uniform in size. Since the dimensions of these pores are such as to accept, for adsorption, molecules of certain dimensions while rejecting those of larger dimensions, these materials are deemed to possess the property of shape selectivity, have been referred to as "molecular sieves", and are utilized in a variety of ways to take advantage of these properties.

Such shape selective zeolites include a wide variety of positive ion-containing crystalline aluminosilicates, both natural and synthetic. Aluminosilicates can be described as a rigid three-dimensional network of $SiO_4$ and $AlO_4$ in which the tetrahedra are cross-linked by the sharing of oxygen atoms whereby the ratio of the total valence of the tetrahedra-containing aluminum is typically balanced by the inclusion in the crystal of a cation, for example an alkali metal or an alkaline earth metal cation. This can be expressed by formula wherein the ration of Al to the number of various cations, such as Ca/2, Sr/2, Na, K, or Li is equal to unity. One type of cation may be exchanged either in entirety or partially by another type of cation utilizing ion exchange techniques in a conventional manner. By means of such cation exchange, it has been possible to vary the size of the pores in a given aluminosilicate by suitable selection of the particular cation. The spaces between the tetradehra are occupied by molecules of water prior to dehydration.

A preferred group of shape selective crystalline aluminosilicates, designated as those of the ZSM-5 type (e.g. see U.S. Pat. No. 3,702,886) is well known for use in the synthesis of olefins from syn gas derived materials such as methanol. Other shape selective zeolite materials are also well known for this purpose as discussed in the aforedescribed patents.

Unfortunately, the use of shape selective zeolites to catalyze methanol and/or dimethyl ether conversion for olefin production is not entirely satisfactory because such zeolites are also well known to catalyze the formation higher hydrocarbons from the initially produced olefins such as $C_5+$ paraffins, naphthenes, aromatics and alkylated aromatics. The particular distribution of products obtained from the use of any given catalyst is typically controlled by the reaction conditions, particularly temperature. Thus, while there is not a clear line of demarcation in product distribution as a function of temperature, it has been recognized (for example see U.S. Pat. No. 3,894,107) that as the reaction temperature is increased, the methanonl conversion can be shifted in favor of the formation of ethers, olefins, aromatics and alkylated aromatics at respectively higher reaction temperatures. The use of temperature control to influence product distribution is illustrated in U.S. Pat. Nos. 4,052,429 and 4,058,576 wherein staging of the reactions is employed. The partial pressure of the reactant feed has also been observed to influence olefin selectivity. Thus, U.S. Pat. No. 4,025,576 discloses the use of a subatmospheric partial pressure of the reactant feed to improve its conversion with enhanced olefin selectivity. Subatmospheric partial pressure of the reactant feed is obtained either by maintaining a partial vacuum in the conversion zone, or by co-feeding a diluent. Suitable diluents include any substantially inert substance that is a gas or vapor at reaction temperature such as steam, as well as nitrogen, carbon dioxide, carbon monoxide, hydrogen, and the like.

While optimization of operating conditions for a given zeolite to optimize a desired product distribution is important, such procedures are limited in the effects which can be produced thereby by inherent limitations in the physical and chemical properties of the zeolite.

Zeolite catalytic properties can be strongly influenced by such factors as crystal morphology, uniformity of crystal morphology, acidity characteristics and silica/alumina mole ratio, cation identity, pore size distribution, degree of crystallinity, as well as by control of numerous process conditions employed during the preparation of the zeolite which in turn can affect one or more of the aforedescribed characteristics in addition to producing indeterminate effects. Thus, the number of permutations and combinations of possible preparative process conditions, and resulting catalyst characteristics, is astronomical. Consequently, one is faced with a seal of variables in attempting to correlate a particular set of catalyst properties, a means for consistently achieving these properties, and the ultimate effect of a given set of properties on catalyst performance.

Furthermore, it will be understood that catalyst performance includes not only catalyst activity, and selectivity to a particular product distribution but also catalyst life.

For example, olefin synthesis reactions inevitably are accompanied by complex side reactions such as aromatization, polymerization, alkylation and the like to varying degrees. As a result of these complex reactions, a carbonaceous deposit is laid down on the catalyst which is referred to by petroleum engineers as "coke". The deposit of coke on the catalyst tends to seriously impair the catalyst efficiency for the principal reaction desired, and to substantially decrease the rate of conversion and/or the selectivity of the process. Thus, it is common to remove the catalyst from the reaction zone after coke has been deposited thereon and to regenerate it by burning the coke in a stream of oxidizing gas. The regenerated catalyst is returned to the conversion stage of the process cycle. The period of use between catalyst regenerations is often referred to as catalyst life. In short, coke deposits are believed to be a primary contributing factor to reductions in catalyst life. There are obvious economic incentives to improve the catalyst life such as the savings in capital investment for regeneration equipment.

As with such catalyst properties as activity and selectivity, one can control catalyst life through control of the operating conditions. However, it would be a significant advantage if catalyst life could be improved by improving the nature of the catalyst itself through its preparative procedure.

Unfortunately, it is very difficult to predict improvements in catalyst performance from variations in conventional methods of synthesis. This stems from the fact that the most conventional way to identify a particular zeolite is by its characteristic X-ray diffraction pattern. However, catalyst performance of two zeolites with the same XRD pattern can differ drastically, in many instances for indeterminate reasons. One is therefore forced to search beyond the XRD pattern of a zeolite capable of enhancing catalyst performance.

The present invention focuses on the combination of active pH control with an acid to adjust the initial pH of the reaction mixture within specifically defined limits, in the presence of sodium cations and at a specifically defined $SiO_2/Al_2O_3$ mole ratio conducive to the synthesis of olefins from methanol.

In the article "Crystallization of Zeolite ZSM-5 From a Single Cation System", by H. Nakamoto, and H. Takahashi, Chemical Letters, pp. 1739–1742 (1981), the authors report the production of a ZSM-5 zeolite in the presence of $TPA^+$ as the only cation, by control of the concentration ratios of $(TPA)_2O/SiO_2$, $SiO_2/Al_2O_3$, and $H_2O/SiO_2$ in the reaction mixture. They conclude that the crystallization rate is strongly dependent on the $(TPA)_2O/SiO_2$ mole ratio and indicate that a minimum ratio of 0.2 is necessary for the formation of ZSM-5 in their system (e.g. $SiO_2/Al_2O_3=100$; Temp.$=150°$ C.; $H_2O/SiO_2=81$; $Na/SiO_2=0.0038$), thereby ensuring sufficient alkalinity in the reaction mixture to induce dissolution of the amorphous solid to form soluble active species from which nuclei grow. Since crystallization was observed to occur rapidly after the induction period for dissolution, the formation of nuclei is suggested as the rate determining, step in the overall process. No crystalline phase is observed after 5 days at a $(TPA)_2O/SiO_2$ ratio of 0.1. Increasing the $SiO_2/Al_2O_3$ ratio increased crystallization independent of whether single $TPA^+$ or binary $Na^+/TPA^+$ system is employed. However at $SiO_2/Al_2O_3$ ratios below 100, the $Na^+/TPA^+$ system achieves better crystallization than the $TPA^+$-system, while at ratios above 100 the Na cation is said not to play an important role in crystallization. Increasing the $H_2O/SiO_2$ ratio was found to decrease the crystallization rate. Finally, as the $(TPA)_2O/SiO_2$ and $SiO_2/Al_2O_3$ ratios were increased in a mono cation $TPA^+$ system, larger well defined crystals were observed to form having a barrel shape. Catalyst performance is not reported for any of the synthesized zeolites.

It is appropriate to mention that Nakamoto et al as well as many of the hereinafter discussed articles mention the "alkalinity" of the reaction mixture. The concept of increasing or decreasing alkalinity is to be distinguished from increasing or decreasing pH. When relatively strong bases such as NaOH or TPAOH are present in the initial reaction mixture, the pH of the same will almost always be 14. Thus, as more base is added while the alkalinity may increase, the initial pH will remain at 14.

For example, while FIG. 1 of Nakamoto et al illustrates increasing alkalinity, the initial reaction mixture pH of all of the runs is 14.

A paper by K. Chao, T. Tasi, and M. Chen, entitled "Kinetic Studies on the Formation of Zeolite ZSM-5", Journal of Chem. Soc. Trans. 1, Vol. 77 pp. 547–55 (1981) (hereinafter Chao et al) discloses the effects on nucleation rate and crystal growth, of varying the initial $SiO_2/Al_2O_3$ ratio, alkalinity, and reaction temperature during zeolite synthesis from $Na^+/TPA^+$ aluminosilicate gels. While sulfuric acid is disclosed as one of the reagents used in the experimental section, neither the amount nor the manner in which it is used is reported. Chao et al propose that alkalinity of the hydrogel affects the nucleation rate through two mechanisms, namely (1) the dissolution of the gel materials and formation of $Al(OH)n$, and (2) the polymerization of dissolved silicate and aluminate ions to form aluminosilicate or polysilicate ions which can act as a source of nuclei. From the data presented, the authors propose that increasing the alkalinity of the reaction mixture (a) increases dissolution of silicate species of the hydrogel, thereby shortening the induction period (i.e increasing nucleation rate), but (b) eventually results in restriction of the aforedescribed polymerization thereby lengthening the induction period at very high alkalinity. Chao et al therefore conclude that to achieve the highest nucleation rate an optimum alkalinity can be established where the dissolution and polymerization phenomenon are maximized. On the other hand, alkalinity is said to have almost no effect on the rate of crystal growth. The $SiO_2/Al_2O_3$ ratio is alleged to have a two fold effect on reaction kenetics, namely, (1) except at low alkalinity, the lower the ratio (i.e. more aluminum) the higher the alkalinity needed to attain the aforedescribed optimum alkalinity point (since aluminum consumes $OH^-$ ions forming $Al(OH)n$) and (2) at low levels of alkalinity, the higher the ratio the faster the crystal growth rate. For an aluminum and sodium free system, excess TPAOH was required to achieve the comparable levels of alkalinity to compensate for omission of sodium hydroxide. The sodium/aluminum free system, however yielded only 16% crystallinity (see Table 3). While alkalinity of the reaction system is discussed in great detail, the initial pH of the reaction mixtures associated with the various alkalinities disclosed is never mentioned. Furthermore, the catalyst performance of the zeolites prepared by Chao et al was never tested and hence there is no correlation between alkalinity and/or initial pH on catalyst performance.

The crystallization kinetics of the $NH_4^+/TPA^+$ system were further studied in the paper "Synthesis and Growth of Zeolite $(NH_4, TPA)$-ZSM-5 " by N. Ghamami, and L. Sand, Zeolites Vol. 3, pp. 155–62 (April 1983) (hereinafter Ghamami et al). The use of ammonium hydroxide is implemented instead of an alkali metal cation to eliminate the need for an ion-exchange step for subsequent conversion of ZSM-5 catalyst to the hydrogen form (e.g. typically $Na_+$ is exchanged for $NH_4^+$ and the resulting material calcined to evolve $NH_3$, to produce H-ZSM-5, and decompose the organic cation). In a system using precipitated silica powder, 25% TPAOH and initial $SiO_2/Al_2O_3=28$, the reaction does not proceed or proceeds slowly. Increasing the initial $SiO_2/Al_2O_3$ ratio to 59 gives successful crystallization. This ratio is then used to explore the effect of varying the $NH_4^+/NH_4^+ + TPA^+$ ratio on crystallization. As this latter ratio is decreased (i.e. by increasing $TPA^+$ and reducing $NH_4^+$ correspondingly) the nucleation and crystallization rates are found to increase. A decrease in the $NH_4^+/NH_4^+ + TPA^+$ ratio also corresponds to an increase in alkalinity which accelerates the reactant dissolution processes. Omitting $NH_4^+$ altogether (i.e., using TPAOH alone) results in spherical crystal aggregates while omitting $TPA^+$ (i.e. using $NH_4OH$ alone) results in an amorphous material (Compositions VI and VII respectively). At 180° C. reaction temperature and a $TPA^+/NH_4^+$ ratio of 5/5, increasing the $SiO_2/Al_2O_3$ ratio of the reaction mixture in the regime of 59; 69; 90 and alumina free, increases the nucleation and crystallization rates. The pH of the reaction mixtures employed in the first part of this paper (i.e. Compositions I to IX) is never reported. In the second part of the paper, TPABr is employed at the $TPA^+$ source, Ludox AS40 (aqueous colloidal silica) as the silica source, and Reheis F-2000 aluminum hydroxide gel powder as the alumina source. The use of an initial $SiO_2/Al_2O_3$ ratio of 59, and TPABr, rather than TPAOH, reduces the alkalinity of the reaction mixture producing an amorphous material at $NH_4OH/TPABr$ ratios of 1.5 to 10 (Composition II). The use of excess $NH_4OH$ (i.e. $NH_4OH/TPABr=15$; Composition XIV) gives a reaction mixture pH of 12–12.5 and produces euhedral crystals after 5 days. When the initial $NH_4OH/TPABr$ ratio is reduced from 15 (in Composition XIV) to 12.5 (Composition XVI) thereby presumably reducing the initial pH to slightly below the 12–12.5 pH value (of Composition XIV), only 50% of the product is crystalline after 5 days.

It is appropriate to mention that the only initial reaction mixture pH reported in Ghamami et al is that of Composition XIV prepared in the absence of sodium. This pH value is not actively controlled (e.g. with acid), but is merely a result of the conditions established from the initial amounts and identity of ingredients selected. The TPABr salt is essentially neutral in terms of its effect on pH, and when a mixture containing a $TPABr/NH_4OH/H_2O$ mole ratio of 8:120:750 was prepared, the pH of this mixture was 14. However, Ludox AS40, which has a pH of 9.2, can influence the initial pH of the reaction mixture.

Likewise Reheis alumina exhibits a pH of 8.6 and its addition to the reaction mixture can also affect the initial pH of the same. Consequently, it has been concluded that the identity of the source of the alumina and silica in Composition XIV of Ghamami et al is responsible for the inherent initial 12.5 pH of the same.

The article, "Preparation of Zeolite Catalyst for Synthesis of Lower Olefins from Methanol" by E. Kikuchi, R. Hamana, S. Hamanaka and Y. Morita, J. of Japanese Petroleum Institute, Vol. 24, pp. 275–280 (1981) (hereinafter Kikuchi et al) discloses the preparation, and testing for methanol conversion, of ZSM-5 catalysts. Kikuchi et al examine two catalysts designated A and B. Catalyst A is prepared in accordance with the standard Mobil ZSM-5 technique of U.S. Pat. No. 3,702,886, using silica gel, $TPA^+$ and $NaAlO_2$. Catalyst B is prepared using water glass (92.9% $SiO_2$, 9% $Na_2O$), aluminum nitrate and $TPA^+$. However, sufficient 1N $HNO_3$ is added to the reaction mixture for Catalyst B to bring the reaction mixture pH to 10–10.5. As the pH is reduced, a gellous solution forms and is stirred. Catalyst samples A and B are then tested for methanol conversion with further testing of Catalyst B at varying $SiO_2/Al_2O_3$ ratios. Comparing Catalysts A and B on a morphological basis, Kikuchi et al report that the size of the crystallites of Catalyst B is about 4 times that of Catalyst A and that the crystallinity of Catalyst B after 1 day of crystallization is about the same as Catalyst A after 6 days. In terms of catalyst performance, Catalyst B is said to show a selectivity to lower olefins about 1.5 times that of Catalyst A at similar conversion levels. Kikuchi et al conclude that the differences in activity may be attributable to a slight difference in pore structure which cannot be identified by XRD, which in turn may enhance the rate of diffusion of the olefin out of the pores. Increasing the $SiO_2/Al_2O_3$ ratio of Catalyst B in the regime of 50; 202; 362; and 602 results in an increase in selectivity to lower olefins, a decrease in the activity of catalyst, and a decrease in the selectivity to aromatic hydrocarbons. Note that Kikuchi et al do not specify whether the $SiO_2/Al_2O_3$ ratios reported are those of the actual zeolite, or the starting ratios employed in the reaction mixture. It is further noted that while Kikuchi et al appear to be the first workers to employ active pH control with an acid, in a sodium cation containing system, the pH to which the reaction mixture was adjusted is confined to 10–10.5 with no recognition of any influence of such control on catalyst life.

European Patent Application 93,519 discloses a process for preparing high silica containing zeolites of the ZSM-5 family wherein a buffer is employed to control the pH of the reaction mixture during crystallization between 9.5 and 12. This process is said to be based on the discovery that the final pH of the reaction mixture, will determine the morphology of the resulting crystals. More specifically, a final pH of 10–10.5 is said to produce rod-shaped crystals, a final pH of 12 to 12.5 twinned short prismatic crystals with near spherulitic morphology, and a final pH of 11 to 12, a morphology intermediate between the above noted morphologies. The reaction mixture which is associated with the above morphologies contains water, a source of quaternary ammonium cations, silica, and an alkali metal. An aluminum source is optional. No utility is disclosed for the zeolites prepared in accordance with this process and consequently the activity of such zeolites was never tested for any purpose. The buffers disclosed at page 3 are conjugate bases, i.e. salts, of a weak acid and a strong base. In contrast, the present invention excludes the presence of buffers from the reaction mixture. Furthermore, the activity of the catalysts of the present invention has been found to be dependent on the initial pH of the reaction mixture and hence there is no need to employ a buffer. Furthermore, there is no recognition of the effect of adjusting the initial pH of the reaction mixture on catalyst life in accordance with the process of the present invention.

U.S. Pat. No. 4,275,047 discloses a process for preparing zeolites such as ZSM-5 wherein the use of alkylammonium ions can be avoided by inclusion in the reaction mixture of a seed zeolite having a specifically defined pore diameter. For unspecified reasons, the reaction mixture is disclosed as preferably containing one or more anions of strong acids, especially chloride, bromide, iodide or sulphate. Such anions can be introduced as an acid, and/or alkali metal, aluminum, ammonium or onium salts. Note also that $H_2SO_4$ is employed in Example 5, it is assumed, as a source of sulphate ions. No initial reaction mixture pH is specified.

In the article "Synthesis and Characterization of ZSM-5 Type Zeolites III, A Critical Evaluation of the Role of Alkali and Ammonium Cations" by Z. Gabelica, N. Blum, and E. Derouane, Applied Catalysis, Vol. 5, pp. 227–48 (1983) (hereinafter Gabelica et al), the role of alkali metal and ammonium cations in the nucleation and growth of ZSM-5 zeolites is studied. The authors conclude that the morphology, size, chemical composition and homogeneity of the crystallites depend on competitive interactions between $TPA^+$ or alkali metal cations and aluminosilicate polymeric anions during early stages of nucleation. The crystallization time of a Na free, $TPA^+/NH_4^+$ based system is reported as 93 days. While both acidic and basic systems are studied, the TPA is added as the bromide salt, and in some instances the pH of the reaction mixture is increased from acidic (e.g. 2-4) to basic (pH 9) by the addition of sodium silicate. One significant observation of Gabelica et al is that the initial $SiO_2/Al_2O_3$ ratio appeared to have little influence on the final zeolite composition, the later being strongly dependent on the nature of the alkali counterion, which in turn affected the size of the crystallites. None of the Gabelica et al zeolites are tested for catalyst performance.

Commonly assigned U.S. patent application Ser. No. 630,723, filed July 13, 1984 by A. Bortinger, W. Pieters, and E. Suciu, is directed to a process for preparing zeolites, e.g. ZSM-5, on an active initial pH controlled basis (i.e. initial pH=9.0 to 12.5) but in the substantial absence of alkali metal cations (e.g. sodium) in the reaction mixture.

From the above discussion it can be seen that except for the above discussed commonly assigned Bortinger et al application, ZSM-5 zeolites have been synthesized with organic cations under controlled processing conditions on a sodium free basis, but in the absence of active initial pH control, although the catalyst performance of such zeolites does not appear to have been tested. On the other hand the use of active initial pH control with an acid has only been applied to sodium-$TPA^+$ binary cation conventional ZSM-5 systems at a pH of 10-10.5 and the resulting zeolite catalyst exhibits good catalyst performance relative to the absence of pH control.

However, to the best of the inventors' knowledge herein, the combination of the use of sodium containing cation reaction system under strict active initial pH controlled conditions (i.e., pH 11.3 to 11.7) bin accordance with the process of the present invention has never been reported, nor has the catalyst performance of zeolites prepared in this manner.

SUMMARY OF THE INVENTION

The present invention is based, inter-alia, on the discovery of the functional relationship between the initial pH of, and the presence or absence of sodium cations, within, the reaction mixture employed for ZSM-5 type zeolite synthesis, and the ultimate zeolite catalyst performance for olefin synthesis. The control of the initial reaction mixture pH is an active control requiring the use and presence of an acid. Furthermore, the use of initial pH control is distinguishable from control of the alkalinity of the reaction mixture in that variations in alkalinity of the reaction mixture do not necessarily result in a variation of the pH of the same. Furthermore, only slight variations of the initial pH can result in drastic variations in catalyst life. The natural alkalinity of conventional reaction mixtures can be influenced by the identity and amounts of the silica source, the alumina source, the organic cation source, dilution, and the type of inorganic salts such as $NH_4Br$. Consequently, the natural alkalinity of the initial reaction mixture will fluctuate uncontrollably in response to changes in one or more such variables.

The amounts and proportions of the components of known sodium containing ZSM-5 producing reaction mixtures are typically not actively controlled with acid to achieve a particular initial pH or to impart a particular catalyst performance. When initial pH control has been employed the pH employed was limited to 10-10.5.

It has been found that the catalyst life of a zeolite prepared in accordance with the process of the present invention can be increased by a factor of about 7.

The present invention relies on the combination of two critical variables, namely, active initial pH control and sodium cation presence, to improve catalyst life. This technique also permits one to control other synthesis process variables independently of the initial pH of the reaction mixture to maximize catalyst performance.

Accordingly, in one aspect of the present invention there is provided a process for producing a crystalline aluminosilicate zeolite, preferably of the pentasil family, e.g. ZSM-5, which comprises:

(1) admixing to form a reaction mixture in the absence of a buffer:
  (a) at least one tetraalkyl ammonium hydroxide, in an amount sufficient to impart a pH to the reaction mixture in the initial absence of said acid of (f) of not less than 13 when measured at room temperature;
  (b) at least one sodium cation source;
  (c) at least one silica source;
  (d) at least one alumina source;
  (e) water; and
  (f) at least one acid
in a manner and under conditions sufficient to (i) impart a $SiO_2/Al_2O_3$ mole ratio of from about 70 to about 2000 to the crystalline zeolite; (ii) impart a $Na_2O/SiO_2$ mole ratio to the admixture of at least about 0.05 and (iii) adjust, with said acid, the initial pH of the reaction mixture, when measured at room temperature, to be from about 11.3 to about 11.7;

(2) heating the reaction mixture until crystals of said zeolite form; and (3) separating said crystals from the reaction mixture.

In another aspect of the present invention there is provided a process for synthesizing olefins using a zeolite prepared in according with the above process, converted to the hydrogen form and calcined.

DESCRIPTION OF PREFERRED EMBODIMENTS

In accordance with the present invention, nitrogeneous aluminosilicate zeolites, preferably of the ZSM-5 type are produced and then optionally converted to the hydrogen form and calcined to render them suitable for olefin synthesis.

More specifically, an aluminum source is reacted with a silica source (a) in the presence of (i) a tetraalkylammonium hydroxide, (ii) a sodium cation source and (b) in an initial pH adjusted reaction mixture.

The aluminum source must be capable of being solubilized in the reaction mixture under reaction conditions. Thus, the alumina source can be an aluminum salt such as aluminum chloride, sulphate, and/or nitrate, or alumina itself, in a form which is, or can be hydrated such as colloidal alumina, gamma alumina or the alpha or beta aluminum trihydrate as well as mixtures of the above.

The preferred alumina source is aluminum nitrate.

The silica source can be of any type having sufficient chemical reactivity to take part in the zeolite synthesis at an adequate rate. Suitably the silica source is an amorphous silica, such as a colloidal silica e.g., available under the tradename Ludox TM which typically contains 20 to 50% w/w silica in aqueous suspension, sodium silicate, fumed silica, precipitated silica, and mixtures of the same. The preferred silica source is sodium silicate.

The tetraalkylammonium hydroxide (TAAOH) suitable for use in the present invention is conventional in the synthesis of zeolite type catalysts and each alkyl group thereof contains typically from about $C_1$ to $C_4$ carbons, preferably about $C_2$ to $C_3$ carbons, and most preferably $C_3$ carbons, including tetrapropyl ammonium, and tetraethyl ammonium. Tetrapropylammonium hydroxide is preferred.

The tetraalkyl ammonium hydroxide, functions as a strong base to achieve the minimum pH of the reaction mixture prior to the acid addition described hereinafter.

The sodium cation source can be any conventional sodium containing reagent typically employed in zeolite synthesis as a source of sodium cations which are incorporated into the zeolite to balance the electrovalence of the aluminum containing tetrahedra of the zeolite. Suitable reagents which can constitute the sodium cation source include sodium silicate which also can constitute the silica source, and sodium hydroxide, which can also function as a base to assist in achieving the minimum pH requirements of the reaction mixture prior to acid addition specified hereinafter. Other sources of the sodium cation include sodium aluminate and sodium salts, such as sodium chloride. The sodium cation source is provided to the reaction mixture to achieve therein a $Na_2O/SiO_2$ mole ratio of at least about 0.05, preferably at least about 0.1 and most preferably at least about 0.3.

The zeolite forming reaction is conducted in accordance with the process of the present invention by heating a suitable aqueous reactant mixture. The initial reaction mixture employed will typically have an initial composition expressed in terms of oxide mole ratios within the following ranges prior to acid addition:

|  | Broad | Preferred | Most Preferred |
| --- | --- | --- | --- |
| $(TAA)_2O/SiO_2$ | 0.01 to 5 | 0.05 to 1 | 0.05 to 0.4 |
| $SiO_2/Al_2O_3$ | 80 to 2200 | 220 to 800 | 220 to 650 |
| $H_2O/SiO_2$ | 10 to 200 | 20 to 140 | 40 to 90 |
| $OH^-/SiO_2$ | 0.02 to 10 | 0.2 to 5 | 0.3 to 3 |
| $H_2O/OH^-$ | 5 to 500 | 10 to 200 | 20 to 175 |
| $Na_2O/SiO_2$ | 0.05 to 5 | 0.1 to 4 | 0.3 to 3 | wherein TAA is the sum of the tetraalkyl ammonium cations.

The admixing of the aforedescribed ingredients typically at room temperature, is controlled to impart to the reaction mixture an initial pH at room temperature (i.e. between 20° and 25° C.) prior to adding acid, of typically not less than about 13, and most preferably about 14. The pH of the reaction mixture is then adjusted by the addition of sufficient strong inorganic acid, to a value of typically from about 11.3 to about 11.7, preferably from about 11.4 to about 11.6 (e.g. 11.5). The term "acid" as used herein in conjunction with pH adjustment is defined to exclude any silica or alumina source with acid properties relative to more basic components employed in the reaction mixture.

Furthermore, by strong acid is meant one that reacts completely with the aqueous solvent to give the conjugate acid of the solvent, i.e. $H_3O_+$. The use of a strong acid avoids the formation of a buffer in the reaction mixture in accordance with EPA No. 93,519. Furthermore, the pH of the reaction mixture during crystallization is not controlled, e.g., with a buffer.

Suitable strong inorganic acids include $HNO_3$, $H_2SO_4$, HCl, and mixtures thereof.

The preferred acid is $HNO_3$. Preferably the acid will decompose during calcination of the zeolite.

Ordinarily, the reaction mixture components are combined by mixing the sodium cation source, the silica source and the tetraalkylammonium hydroxide, to form an aqueous solution to which is added the alumina source and the resulting mixture then adjusted for pH with acid.

However, it is also possible, for example, to mix the acid with the alumina source followed by addition of the silica source to give a very low pH of about 1. The TPAOH is then added to achieve the appropriate initial reaction mixture pH and composition as described above.

It will be noted, however, that the amount of base to be employed in conjunction with the other reagents to meet the compositional requirements specified hereinabove, and the initial pH imparted thereby to the reaction mixture in the absence of an acid, will dictate and control the amount of acid employed to achieve the ultimate initial pH, regardless of whether the pH is approached from the high or low end of the pH scale. Consequently, and in view of the above, whether the ultimate initial pH of the reaction mixture is approached from the high or low end of the pH scale, either contingency is considered herein to be an active adjustment of pH with an acid.

The pH adjusted reaction mixture is placed in a closed container, such as teflon lined autoclave and heated, typically to a temperature of from about 100 to about 220, preferably from about 120 to about 190, and most preferably from about 140 to about 165° C., until completion of the crystallization, e.g., for a period of typically from about 1 to about 10, preferably from about 3 to about 8, and most preferably from about 4 to about 6 days. Generally a minimum of about 3 days, preferably 6 days is needed for complete crystallization. Periods in excess of 6 days are of no apparent advantage.

While crystallization can be conducted at atmospheric, subatmospheric, or superatmospheric pressures in air, it is preferred, to replace the air in the reaction vessel with an inert gas, such as nitrogen under a pressure of from 5 to 100 psi, to avoid possible oxidation of the organic base.

Preferably, the reaction mixture is stirred during all or part of the crystallization period. The degree of agitation is not critical but typically is sufficient to uniformly mix the contents of the reaction mixture (e.g. about 650–1000 rpm).

Upon completion of crystallization from the reaction mixture, the product crystals are separated, as by cooling and filtering, and are water washed and dried at a temperature of typically from about 80° to about 120° C.

To be suitable for olefin synthesis, the zeolite obtained will preferably possess a $SiO_2/Al_2O_3$ mole ratio of at least 70 (e.g. at least 100), typically from about 70 to about 2000 (e.g., 100 to 1000), preferably from about 200 to about 800, and most preferably from about 200 to about 650 (e.g. 200 to 350). As a general rule it has been found that the final $SiO_2/Al_2O_3$ mole ratio will vary typically from about 10 to about 60% of the initial starting ratio.

The process of the present invention is applicable to the preparation of zeolites which employ a tetraalkylammonium hydroxide base including ZSM-5 (U.S. Pat. No. 3,702,886); ZSM-11 (U.S. Pat. No. 3,709,979); and ZSM-12 (U.S. Pat. No. 3,832,449); the disclosures of said patents being herein incorporated by reference.

The resulting zeolites which contain a mixture of organic and sodium cations are catalytically inactive for the methanol to olefin reactions. To activate the zeolite, the same is converted to the hydrogen form by conventional techniques. Thus, typically, the sodium cations are first replaced with an intermediate cation, such as by ammonium ion exchange, e.g. using ammonium nitrate, which is convertable to the hydrogen cation upon calcination.

The zeolite is then activated for a time effective to convert the zeolite to the hydrogen cation form by calcination at a temperature of typically from about 400° to about 900°, preferably from about 450° to about 750°, and most preferably from about 500° to about 600° C., preferably in air. Typical calcination times can vary from about 2 to about 15 hours (e.g. 5 to 10 hours). Conventional exchange procedures may result in a residual sodium ion content in the exchanged zeolite of from about 20 to about 100ppm.

The zeolite catalyst is adaptable to use in the various psychical forms in which catalysts are commonly used as particulate material in a contact bed, or a coating material on monolithic structures generally being used in a form to provide high surface area. The catalyst, can if desired, be composited with various catalyst binder or support materials which do not adversely affect the catalyst or the reactions in which the catalyst is to be employed. Representative matrix materials are disclosed in U.S. Pat. No. 4,025,571 at Col. 9, the disclosure of which is herein incorporated by reference.

The reactions conducted in accordance with the use of the zeolites prepared in accordance with the process of the present invention are well known for synthesizing olefins. Such reactions can be broadly characterized by the condensation of certain feed materials to form hydrocarbon mixtures rich in light olefins, e.g., $C_1$ to $C_5$, especially ethylene and propylene. Suitable feeds for this reaction include any monohydric alcohol having from 1 to 4 carbon atoms and/or ethers derived from these alcohols. Thus methanol, ethanol, n-propanol, isopropanol, n-butanol, sec-butanol and isobutanol may be used either alone or in admixture with one another, or in admixture with ethers derived from such alcohols. Likewise, as noted, ethers such as methylethyl ether and dimethyl ether may be similarly used. Particularly preferred feeds are methanol, dimethyl ether and mixtures thereof.

The alcohol employed in the feed may be manufactured from synthesis gas, i.e., a mixture of CO and $H_2$, from coal, by fermentation, by manufacture from a petroleum fraction in excess supply, or any other suitable means.

More specifically, the process of this invention for using the zeolite herein is preferably conducted such that alcohol and/or ether conversion is carried out in the vapor phase by contact in a reaction zone, such as for example, a fixed bed of catalyst, under effective conversion conditions, said catalyst being characterized as above-defined.

The alcohol and/or ether hydrocarbon conversion process described herein also may be carried out as a batch-type, semi-continuous or continuous operation utilizing a fixed or moving (e.g. fluidized) bed catalyst system. Thus, one embodiment entails use of a catalyst zone wherein the alcohol and/or ether charge is passed concurrently or countercurrently through a moving bed of particle-form catalyst. The latter, after use may be conducted to a regeneration zone wherein coke is burned from the catalyst in an oxygen-containing atmosphere, e.g. air, at an elevated temperature, after which the regenerated catalyst is recycled to the conversion zone for further contact with the alcohol and/or ether feed.

The hydrocarbon feed gas may optionally also contain diluents including any substantially inert substance that is a gas or vapor at reaction temperature. Gaseous nitrogen, carbon dioxide, and carbon monoxide are examples of such materials. Alkanes having up to 3 carbon atoms such as methane, ethane and propane may also be employed as diluents, while $C_4$ and higher carbon number alkanes are undesirable since they are more rapidly converted to coke.

Other hydrocarbon feed additives, which can be used in conjunction with an alcohol, e.g. methanol feed, are aromatic hydrocarbons. Such aromatic hydrocarbon compounds include benzene, $C_1$ to $C_5$ (e.g. $C_1$ to $C_2$) alkyl mono or poly substituted benzenes, para-xylene, toluene, and mixtures thereof. The aromatic hydrocarbon promoters are chosen to be of such a size as to be adsorbed into and diffuse within the zeolite pores. While they preferably are reactive towards Bronsted acids they should not irreversibly neutralize the same. The preferred aromatic promoters include benzene, para-xylene and toluene.

The mole ratio of aromatic hydrocarbon to methanol will typically vary from about 0.2:1 to about 0.01:1, preferably from about 0.1:1 to about 0.02:1, and most preferably from about 0.07:1 to about 0.04:1.

Water in the form of steam can also be included in the feed containing the alcohol and aromatic hydrocarbon at a molar ratio of alcohol to water of typically from about 1:0.05 to about 1:0.7, preferably from about 1:0.3 to about 1:0.5; and most preferably from about 1:0.1 to about 1:0.2.

When dimethyl ether is employed as the reactant in the feed gas either in the presence, and particularly in the absence of methanol, it is preferred to initially include steam in the feed gas. More specifically, the molar ratio of dimethyl ether to steam is typically controlled to be from about 1:5 to about 1:0.2, preferably from about 1:2 to about 1:0.5, and most preferably from about 1:0.7 to about 1:1.2 for a period of typically from about 2 to about 24, preferably from about 4 to about 10, and most preferably from about 5 to about 8 hours, under the hereindescribed reaction conditions. It is most preferred that the catalyst be contacted first with steam alone for a period of typically from about 1 to about 10, and preferably from about 2 to about 5 hours at the hereindescribed reaction temperatures and conditions. It is believed that initial contact of the zeolite with large amounts of DME in the hydrocarbon feed in the absence of water tends to diminish catalyst life by hastened coke deposition. Alternatively, where a mixture of methanol and DME is employed in the reaction feed, it is preferred, in lieu of the initial steam treatment, to optionally initially introduce methanol alone, for the aforedescribed steam conditioning periods, prior to introducing the methanol/DME feed mixture.

When methanol alone is employed as the reactant in the feedstream in the absence of an aromatic promoter, it is preferred to exclude the presence of steam therefrom.

The temperature at which the alcohol and/or ether hydrocarbon conversion process is conducted should be minimized to limit the rate of coke build-up. Accordingly, the temperature of the reaction zone typically will vary from about 250° to about 500°, preferably from about 300° to about 450°, and most preferably from about 320° to about 360° C.

The feed may be passed over the catalyst at a contact time with the catalyst sufficient to achieve a WHSV of typically from about 2 to about 10, preferably from about 2 to about 7, and most preferably from about 2.5 to about 4 $hr^{-1}$. The reaction pressure typically will be controlled to be about 1 atmosphere. Excessively high pressures alter reaction rates and product selectivity and coking increases significantly.

It is particularly desired to use conditions in the specified ranges that produce conversion to a hydrocarbon mixture comprising a major mole fraction of olefins.

The reaction product effluent from the hydrocarbon conversion process of the present invention contains a hydrocarbon mixture particularly rich in the light olefins, ethylene and propylene, as well as some aromatic hydrocarbons. Generally, a major fraction of the total olefins, calculated on a carbon basis, is ethylene plus propylene. The predominant aromatic hydrocarbons are monocyclic hydrocarbons, notably $C_8$ and $C_9+$ aromatics. Thus, the predominant hydrocarbons are separated from one another by methods well known in the art.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, conversion, selectivity, and yield are calculated on a % carbon basis as follows:

$$\text{Selectivity (\%)} = \frac{n\,C_n}{\sum_{1 \to i} n\,C_n} \times 100$$

wherein $C_n$ is a hydrocarbon product (excluding dimethyl ether) having n carbon atoms and i is the maximum number of carbon atoms of any compound in the product.

$$\text{Conversion (\%)} = \frac{\text{total no. of carbon atoms in product}^*}{\text{total no. of carbon atoms in feed}} \times 100$$

*product excludes dimethylether from methanol $$\text{Yield (\%)} = \frac{\text{selectivity} \times \text{conversion}}{100}$$

In the following Examples and Comparative Examples, unless otherwise specified, zeolite synthesis is conducted in a Parr ™ autoclave equipped with a Teflon liner. The liner is cleaned with HF acid prior to each synthesis. Furthermore, prior to sealing the autoclave for each run, the air present therein is purged by flushing with nitrogen and the autoclave then pressurized to 50 to 100 psi with the $N_2$.

Unless otherwise specified, the testing of the zeolites prepared as described hereinafter is conducted in a tube reactor comprising a stainless steel tube having the dimensions: length 36 cm, O.D. 1.27 cm, and I.D. 1.0 cm. The tube is employed in a verticle position. Across the bottom opening thereof is placed a wire mesh screen on top of which is placed glass wool. About 1 cc of inert alumina particles ($-30+80$ mesh U.S. sieve series) are placed on top of the glass wool. About 1 g of each zeolite tested is then inserted on top of the glass wool and covered with the same, followed by about 1cc of alumina particles, on top of which is placed more glass wool. The reactant feed is passed through the top of the reactor and the products collected from the bottom. Reactor effluent samples are analyzed by on line gas chromatography (G.C.) at the designated on-stream times. Inlet lines to the reactor are placed in a hot box where any liquid feed is vaporized. The reactor is heated in a radiant I.R. furnace and the reaction temperature is determined from thermocouples placed in the upper zone of alumina particles.

Zeolite characterization data obtained for the zeolite samples discussed hereinafter include $SiO_2/Al_2O_3$ mole ratio; % crystallinity obtained through XRD-analysis, acidity equivalents, surface area, average crystal size.

Unless otherwise specified herein, the initial $SiO_2/Al_2O_3$ mole ratio reported at Table 1 is derived from calculations based on the amount of initial materials employed in the synthesis. The final $SiO_2/Al_2O_3$ mole ration is based on elemental analysis.

The % crystallinity XRD-data was collected on a Phillips ADP-3600 diffractometer using CuK radiation at 45KV, 40MA. Prior to analysis, the samples were placed in a constant humidity atmosphere over a saturated $CaCl_2$ solution. Each sample was scanned in the range $4° < 2° < 100°$. The same treatment was provided for the "standard", and data were collected prior to the other analyses so that direct comparison of intensities could be made.

When the scans were completed, the measured counts for eight peaks in each sample were ratioed to the measured counts for the standard, $(I_{SPL}/I_{STD}) \times 100$. These eight values were subsequently averaged to give the "crystallinity".

Catalyst acidity measurements described herein area determined by measuring the ammonia adsorption of a catalyst sample on a Perkin Elmer TGS-II thermogravimetric analyzer using the following procedure:
1. Tare a clean dry platinum sample pan.
2. Add sample (10–20mg) to the pan and place the pan on the TGS-II balance.

3. Set a flow of 40 ml/min of dry, ultrapure $N_2$ through the top section of the balance and 30 ml/min of the same $N_2$ through the sample chamber.
4. Heat the sample to 500° C. in $N_2$ for 30 minutes to dry it and desorb any materials.
5. Set the furnace temperature to a value of 325° C. at which a measurement is desired.
6. Allow the sample to come to a constant weight in the dry $N_2$ atmosphere and record the weight.
7. Change the gas flowing through the sample chamber to 2% $NH_3$ in $N_2$ with a flow rate of 30 ml/min.
8. Allow the sample to come to a constant weight and record the weight.
9. Wt., % $NH_3$ adsorbed=

$$\frac{\text{wt. in } NH_3 - \text{wt. in } N_2}{\text{wt. in } N_2} \times 100$$

Surface area is determined by the BET method using nitrogen as the adsorbent.

Average crystal size determinations are made from the SEM photographs. More specifically, powder samples were dispersed ultrasonically in a 0.1% ethyl alcohol solution. The prepared samples were then drawn onto cover slips affixed to Al analysis mounts. Gold was next sputtered onto the surfaces to provide conductivity in the SEM. A JSM-U3 scanning electron microscope marketed by JEOL (USA), Inc. of Peabody, Ma was used to produce a magnification series from a representative area of each sample. A 45° tilt angle was imposed during the microscopy phase of study. Each micrograph bears a magnification "micron bar" to enable crystal size determination calculations.

Furthermore, unless otherwise specified flow rates expressed as ml/hr (e.g. of methanol) represent the volume of liquid per hour. Flow rates expressed as ml/min represent the volume of a gas per minute. A 1 gram sample of catalyst is always employed in the reactor unless otherwise specified.

In the Examples and Comparative Examples, when a flow rate is specified for an alcohol containing feed during start-up, the same flow rates are employed for producing product analyzed, unless otherwise specified. All catalyst samples were calcined in accordance with Example 1, Part A, unless otherwise specified. All SEM photographs are of calcined material. Unless otherwise specified, on-stream time is measured starting at initiation of start-up; when start-up employs steam only, the on-stream time is measured starting at completion of start-up.

EXAMPLE 1

Part A

Sodium silicate (52 g) (DuPont #9), containing 29% $SiO_2$, was mixed with 24.8 g n-tetrapropyl ammonium hydroxide (25% TPAOH in water). To this solution was added 34 ml $H_2O$ followed by the addition of a solution of 0.448 g $Al(NO_3)_3$ $9H_2O$ dissolved in 8 ml $H_2O$. This mixture was placed in a Teflon liner and the pH was adjusted to 11.5 with 1N $HNO_3$. The teflon liner was placed in an autoclave and was charged with 50 psig $N_2$. The autoclave was heated to 150° C. for 6 days with stirring at a rate of 1000 rpm.

The autoclave was then cooled down to room temperature and the solid product was filtered and washed with 800 ml distilled water.

The product was then dried in the vacuum oven at 120° C. for 16 hours and then calcined for 5 to 10 hours at 550° C. with a stream of air (20 ml/min). The calcined product was then ion exchanged with 250 ml 1N $NH_4NO_3$. The product was then filtered and washed with water. The ion exchange procedure was repeated 3 times. At the end of the exchange, the product was dried in the vacuum oven and again calcined as described above. Catalyst characterization data is provided at Table 1, Run 1.

Part B

About 1 g of the catalyst from Part A of this example having a −30+80 mesh sieve size (U.S. sieve series) was loaded into the reactor and subjected to the following start-up procedure. Steam at a temperature of 260° C. was passed over the catalyst for a period of 60 minutes while gradually increasing the temperature thereof to 335° C.

Part C

Upon completion of start-up a methanol (WHSV 3.5 $hr^{-1}$) and $N_2$ (20 ml/min) feed was passed through the reactor at 335° C. for 120 hours. Product samples were removed at the on-stream times (beginning at start-up completion) shown at Table 1, Runs 1 to 5, analyzed, and the results summarized therein.

COMPARATIVE EXAMPLE 1

Part A

This comparative example, is intended to illustrate the effect of a preparative procedure using an initial pH adjustment to 10–10.5 and wherein the sodium is derived from the use of water glass (29% $SiO_2$, 9% $Na_2O$) as the silica and sodium source. Where possible, an attempt was made to follow the teachings of Kikuchi et al without defeating the primary purpose of the comparative example. Thus, a 1 day crystallization time with stirring (as per Kikuchi et al) was used. Furthermore, Kikuchi et al are silent regarding the preparation of Catalyst B, as to whether calcination was employed; if it was employed what the conditions of calcination were; as well as the sequence of any calcination in relation to the cation exchange procedure, e.g., cation exchange before or after calcination. Ammonium nitrate was employed for cation exchange rather than HCl as per Kikuchi et al. Since the zeolite is essentially inactive without calcination, it was decided to employ a calcination temperature in accordance with Example 1, i.e. 550° C. Furthermore, calcination was conducted before and after cation exchange. Accordingly, 52 g sodium silicate (DuPont #9), containing 29% $SiO_2$, was mixed with 24.8 g n-tetrapropyl ammonium hydroxide (25% TPAOH in water). To this solution was added 34 ml $H_2O$ followed by the addition of a solution of 0.224 g $Al(NO_3)_3$ $9H_2O$ dissolved in 8 ml $H_2O$. This mixture was placed in a Teflon liner and the pH adjusted to 10–10.5 with 1N $HNO_3$. The teflon liner was placed in an autoclave and was charged with 50 psig $N_2$. The autoclave was heated to 150° C. for 1 day with continuous stirring at 1000 rpm.

The autoclave was then cooled down to room temperature and the solid product was filtered and washed with 800 ml distilled water.

The product was then dried in a vacuum oven at 120° C. for 16 hours and then calcined for 5 to 10 hours at 550° C. with a stream of air (20 ml/min). The calcined product was then ion exchanged with 250 ml 1N NH₄NO₃. The product was then filtered and washed with water. The ion exchange procedure was repeated 3 times. At the end of ion exchange, the product was filtered, dried in the vacuum oven and calcined as described above.

Zeolite characterization data are provided at Table 1, Run 6.

Part B

The catalyst from Comparative Example 1, Part A was loaded into the reactor and subjected to the start-up procedure as per Example 1, Part B with the exception that the catalyst was stabilized at 335° C. for an additional 60 minutes during the steam treatment.

Part C

Upon completion of start-up, the steam was substituted for a feed containing methanol (3.5 ml/min) and N₂ (20 ml/min), which was passed over the catalyst at 335° C. for about 18 hours. Due to problems with the G.C. analyzer, the run was aborted.

Part D

The catalyst from Comparative Example 1, Part C, was regenerated using a gaseous mixture of air (30 ml/min) and N₂ (30 ml/min) at 450° C. The regeneration procedure was employed for 18 hours. Upon completion of regeneration, the catalyst was subjected to start-up, in steam as per Example 1, Part B. Upon completion of start-up a methanol/toluene feed (9:1 V/V) was passed over the catalyst at a WHSV of 3.5 hr⁻¹ at 335° C. for 70 hours. No data is reported herein for this run.

Part E

The catalyst from Comparative Example 1, Part D, was again regenerated as per Part D, subjected to start-up as per Example 1, Part B, and the catalyst tested using a methanol/N₂ feed as per Comparative Example 1, Part C at 335° C. Product samples were removed, at the on-stream times (measured from completion of start-up) shown at Table 1, Runs 6 and 7, analyzed, and the result summarized therein.

COMPARATIVE EXAMPLE 2

Part A

Comparative Example 1, Part A (e.g. TPA+/NA+; pH 10.5) was repeated with the exception that: the batch size was reduced in half by reducing the amount of each reaction mixture component in half, crystallization time was increased from 1 to 6 days, and no stirring was employed. Catalyst characterization data is provided at Table 1, Run 8.

Part B

The zeolite prepared in accordance with Comparative Example 2, Part A, was tested in accordance with Example 1, Parts B and C. The total on-stream time was 90 hours measured from completion of start-up. The results of product analysis are summarized at Table 1, Runs 8 to 11 at the indicated on-stream times measured from completion of start-up.

EXAMPLE 2

Part A

The sample of catalyst prepared and tested in accordance with Example 1, Parts B and C was regenerated, after the 120 hours on-stream time use in Example 1, Part C, in accordance with the regeneration procedure of Comparative Example 1, Part D.

Part B

The regenerated catalyst of Example 2, Part A, was subjected to start-up as per Example 1, Part B.

Part C

Upon completion of start-up the catalyst performance was tested in accordance with Example 1, Part C, with the exception that the methanol feed employed therein was replaced with a feed containing methanol and toluene (WHSV=3.5 hr⁻¹) at a methanol:toluene volume ratio thereof of 9:1, together with N₂ (20 ml/min). The results of product testing are summarized at Table 1, Runs 12 to 16.

COMPARATIVE EXAMPLE 3

This comparative example is intended to provide a basis for comparison with Example 2, using a sodium based preparation representative of Kikuchi et al (pH 10.5) but using a 6 day crystallization time in the absence of stirring.

Accordingly, the sample of catalyst tested in Comparative Example 2 was regenerated, after the 90 hours on-stream time of Comparative Example 2, as per Comparative Example 1, Part D, subjected to start-up as per Example 1, Part B, tested in accordance with Example 2, using the same methanol:toluene (9:1) V/V, N₂, feed and flow rates. The results are summarized at Table 1, Runs 17 to 19.

COMPARATIVE EXAMPLE 4

This comparative example is intended to illustrate the performance of catalyst prepared in the absence of sodium using a mono TPA+ cation at an initial pH of 11.5.

Part A

Accordingly, 15.21 g colloidal silica Ludox AS40 (containing 40% SiO₂) were mixed with 45 g N-tetrapropyl ammonium hydroxide (25% TPAOH in water). To the first solution was then added a solution of 0.21 g Al(NO₃)₃ 9H₂O dissolved in 5 ml H₂O. The pH of the mixture was then adjusted with 1N HNO₃ from a pH of 14 to a pH of 11.5. The mixture was then placed in a Teflon liner in a 300 ml Fliutron autoclave equipped with a stirrer. The autoclave was heated to 150° C. and stirred for the first 24 hours of crystallization at 650 rpm and the crystallization for the next 5 days was conducted in the absence of stirring. The autoclave was then cooled down to room temperature and the solid product was filtered and washed with 800 ml distilled water. The product was then dried in the vacuum oven at 120° C. for 16 hours and then calcined at 550° C. with a stream of air flowing at a rate of 20 ml/min for 5 to 10 hours.

Part B

The calcined catalyst from Comparative Example 4, Part A was loaded into the reactor and subjected to start-up as per Example 1, Part B in steam. Upon completion of start-up, the steam was substituted for a methanol/benzene (9:1 V/V) feed mixture containing 4 wt. % H₂O. This feed mixture, flowing at a WHSV of about 3.7 hr⁻¹ was mixed with N₂ (20 ml/min) and the resultant mixture passed through the reactor at a temperature of 335° C. for 250 hours. No data is reported herein for this run.

Part C

The catalyst from Comparative Example 4, Part B was then regenerated as per Comparative Example 1, Part D, subjected to start-up in steam as per Example 1, Part B, and again contacted with the methanol/benzene/water/N$_2$ feed of Part B above, the methanol/benzene/H$_2$O mixture being introduced at a WHSV of 5.25 hr$^{-1}$. The reaction temperature on-stream time profile (measured from completion of start-up) for this run was as follows:
350° C./0 to 15 hours
355° C./16 to 87 hours
365° C./88 to 96 hours
No data is reported herein for this run.

Part D

The catalyst from Part C, above, was regenerated as per Comparative Example 1, Part D, subjected to start-up as per Example 1, Part B, and Part C of Comparative Example 4 repeated using a methanol/benzene/H$_2$O WHSV of 7 hr$^{-1}$ and the following temperature/on-stream time profile:
350° C./0 to 20 hours
365° C./21 to 48 hours
No data is reported for this run. The catalyst was regenerated as per Part D of this comparative example and stored for 4 weeks.

Part E

The catalyst from Part D (after storage) was then again regenerated as per Comparative Example 1, Part D, and subjected to start-up as per Example 1, Part B. Upon completion of start-up a feed mixture of phenol/methanol (1:0.34 W/W) (WHSV 3.5 hr$^{-1}$) was mixed with N$_2$ (20 ml/min) and the resultant feed passed through the reactor at 335° C. for 20 hours. Problems with the G.C. forced termination of this run.

Part F

The catalyst was regenerated as per Comparative Example 1, Part D, with the exception that duration of the regeneration was 65 hours at 450° C. The catalyst was then subjected to start-up as per Example 1, Part B. A methanol/toluene feed (2:1 molar; WHSV 3.5 hr$^{-1}$) was mixed with N$_2$ (20 ml/min) and passed through the reactor at 335° C. for 49 hours. No data is reported herein.

Part G

The catalyst from Part F, was then regenerated as per Comparative Example 1, Part D, subjected to start-up as per Example 1, Part B, and the run of Part F repeated for 24 hours at 335° C. No data is reported herein.

Part H

The catalyst from Part G was then regenerated for 65 hours at 450° C. as per Comparative Example 1, Part D, subjected to start-up as per Example 1, Part B, and the run of Part F was repeated for 20 hours using a phenol/methanol (1:4 molar ratio) feed mixture with N$_2$ (20 ml/min). No data is reported herein.

Part I

The catalyst from Part H was then regenerated, subjected to start-up as per Part H, and the run of Part H repeated for 16 hours using a phenol/methanol (1:1 molar) mixture and N$_2$ (20 ml/min). A feed pump malfunction forced the run to be aborted. No data is reported for this run. The catalyst was therefore regenerated as per Comparative Example 1, Part D and stored for 4 weeks.

Part J

The catalyst from Part I was taken out of storage, loaded into the reactor and subjected to start-up as per Example 1, Part B. A feed of methanol (WHSV=3.5 hr$^{-1}$) was then mixed with N$_2$ (20 ml/min) and the resultant mixture passed through the reactor at a temperature of 335° C. Product samples were removed at the on-stream times shown at Table 1 (measured upon completion of start-up), Runs 20 to 21, analyzed, and the results reported therein.

Discussion of Results

(A) Catalyst Performance

Referring to the runs of Example 1 it can be seen that conversion is maintained at 100% up to an on-stream time of 92 hours and is still very high (92%) after 113 hours on-stream time. In contrast, referring to the runs of Comparative Example 1, based on Kikuchi et al at a pH of 10.5 it can be seen that conversion has dropped to 88% after only 7 hours and degrades quickly thereafter to 58% after only 22 hours on-stream time. Considering the 88% conversion of Run 6 (7 hours on-stream) to be approximately equal to the 92% conversion of Run 5 (113 hours on-stream), the catalyst life has been increased by a factor of about 7 by controlling the initial pH to be 11.5 rather than 10.5.

Referring to the runs of Comparative Example 2 which employ the same crystallization time as Example 1 of 6 days and an initial pH of 10.5, it can be seen that this catalyst also quickly deactivates to a conversion of 10% after only 19 hours on-stream time.

Example 2 and Comparative Example 3 employ the same catalyst as Example 1 and Comparative Example 2, respectively, but conduct the reaction in the presence of a feed containing methanol and toluene. As can be seen from a comparison of Run 4 (Example 1; methanol feed) versus Run 15 (Example 2; methanol/toluene feed) the use of the methanol/toluene feed increases the catalyst life slightly, such that the conversion is 100% after 109 hours on-stream time (Run 15) versus 96% conversion at 108 hours on-stream time (Run 4).

In contrast, the methanol/toluene feed has almost no effect on catalyst life for the catalyst of Comparative Example 2 and Comparative Example 3; the conversion at 11 hours on-stream time being 61T with methanol (Run 10) versus 60% with methanol/toluene (Run 19) at the same on-stream time. Thus the catalyst of the present invention (pH 11.5) is more responsive to the inclusion of an aromatic hydrocarbon in terms of increased catalyst life, than a catalyst prepared at an initial pH of 10.5. Note further the drastic increase in catalyst life from a catalyst prepared at an initial pH of 11.5 (Runs 12 to 16), e.g. 92% conversion at 111 hours on-stream time (Run 16) using a methanol/toluene feed, versus a catalyst prepared at an initial pH of 10.5 (Runs 17 to 19) using the same methanol/toluene feed, e.g. 60% conversion after 11 hours on-stream time (Run 19).

Comparative Example 4 is included to illustrate the performance of a catalyst prepared in accordance with U.S. patent application Ser. No. 630,723, filed July 13, 1984, and at an initial pH of 11.5 but in the absence of sodium. As can be seen from Runs 20–21 the catalyst life of the catalysts of the present invention is significantly increased over the sodium free preparation.

(B) Catalyst Morphology

Observed in these examples are illustrate effects on morphology of including sodium in the preparation at varying initial reaction mixture pH's. Thus, in the absence of stirring and at a pH of 10.5 the crystals appear spherulitic. In the presence of stirring and at the same pH the same morphology is observed but the spherulites are much smaller in diameter. Spherulites similarly sized to those observed at a pH of 10.5 in the presence of stirring are observed at a pH of 11.5 in the presence of stirring. However, when the crystals existing at a pH of 11.5 with stirring are observed under a magnification of 10,000X, what initially appeared to be spherulites under 2000X, now appear as crystalline aggregates. Thus, a distinct change in morphology appears to occur in going from a pH of 10.5 to 11.5 in the presence of sodium. This change in morphology is accompanied by significant change in catalyst performance, namely, catalyst life.

Also observed was a zeolite prepared at an initial reaction mixture pH of 11.5 but in the absence of sodium. This zeolite can be described as being comprised of compound crystals having (i) a primary morphological component characterized as orthorhombic wherein the major exposed and opposed planes possess a hexagonal configuration, and (ii) one or more secondary morphological components characterized as orthorhombic wherein the major exposed and opposed planes possess a rectangular configuration; one face of the major exposed plane of the second morphological component being common with, and wholly subsumed within the major exposed plane of the primary morphological component. This configuration is very unlike the morphology of the zeolites of the present invention.

TABLE 1

| 1 RUN NO. | 2 CORRESPONDING EX. OR COMP. EX. NO. | 3 SEM FIG. NO. | 4 CATION SOURCE | 5 INITIAL REACTION MIXTURE pH | 6 CRYSTALLIZATION TIME* (DAYS) | 7 CRYSTALLIZATION TEMP. (°C.) | 8 INITIAL REACTION MIXTURE $SiO_2/Al_2O_3$ MOLE RATIO | 9 FINAL $SiO_2/Al_2O_3$ MOLE RATIO | 10 XRD CRYSTAL-LINITY (%) | 11 AVG. SEM CRYSTAL SIZE (MICRONS) | 12 ACIDITY EQ. (mm/g) | 13 SA (m²/g) |
|---|---|---|---|---|---|---|---|---|---|---|---|---|
| 1 | Ex. 1 | 1A,B | TPA⁺/Na⁺ | 11.5 | 6(S) | 150 | 400 | 302 | N/A | 2-4 | N/A | N/A |
| 2 | Ex. 1 | 1A,B | TPA⁺/Na⁺ | 11.5 | 6(S) | 150 | 400 | | | | | |
| 3 | Ex. 1 | 1A,B | TPA⁺/Na⁺ | 11.5 | 6(S) | 150 | 400 | | | | | |
| 4 | Ex. 1 | 1A,B | TPA⁺/Na⁺ | 11.5 | 6(S) | 150 | 400 | | | | | |
| 5 | Ex. 1 | 1A,B | TPA⁺/Na⁺ | 11.5 | 6(S) | 150 | 400 | | | | | |
| 6 | C. Ex. 1 | 2 | TPA⁺/Na⁺ | 10.5 | 1(S) | 150 | 400 | 242 | 102 | 2-4 | N/A | 368 |
| 7 | C. Ex. 1 | 2 | TPA⁺/Na⁺ | 10.5 | 1(S) | 150 | 400 | | | | | |
| 8 | C. Ex. 2 | 3 | TPA⁺/Na⁺ | 10.5 | 6 | 150 | 400 | 242 | 97 | 12-16 | N/A | 337 |
| 9 | C. Ex. 2 | 3 | TPA⁺/Na⁺ | 10.5 | 6 | 150 | 400 | | | | | |
| 10 | C. Ex. 2 | 3 | TPA⁺/Na⁺ | 10.5 | 6 | 150 | 400 | | | | | |
| 11 | C. Ex. 2 | 3 | TPA⁺/Na⁺ | 10.5 | 6 | 150 | 400 | | | | | |
| 12 | Ex. 2 (M/T) | 1A,B | TPA⁺/Na⁺ | 11.5 | 6(S) | 150 | 400 | 302 | N/A | 2-4 | N/A | N/A |
| 13 | Ex. 2 (M/T) | 1A,B | TPA⁺/Na⁺ | 11.5 | 6(S) | 150 | 400 | | | | | |
| 14 | Ex. 2 (M/T) | 1A,B | TPA⁺/Na⁺ | 11.5 | 6(S) | 150 | 400 | | | | | |
| 15 | C. Ex. 3 (M/T) | 1A,B | TPA⁺/Na⁺ | 11.5 | 6(S) | 150 | 400 | 202 | 97 | 12-16 | N/A | 337 |
| 16 | C. Ex. 3 (M/T) | 1A,B | TPA⁺/Na⁺ | 11.5 | 6(S) | 150 | 400 | | | | | |
| 17 | C. Ex. 3 (M/T) | 3 | TPA⁺/Na⁺ | 10.5 | 6 | 150 | 400 | | | | | |
| 18 | C. Ex. 3 | 3 | TPA⁺/Na⁺ | 10.5 | 6 | 150 | 400 | | | | | |
| 19 | C. Ex. 3 | 3 | TPA⁺/Na⁺ | 10.5 | 6 | 150 | 400 | 296 | 101 | 2.5-3.0 | 53 | N/A |
| 20 | C. Ex. 4 | 4 | TPA⁺ | 11.5 | 6(S) | 150 | 350 | | | | | |
| 21 | C. Ex. 4 | 4 | TPA⁺ | 11.5 | 6(S) | 150 | 350 | | | | | |

| 1 RUN NO. | 2 CORRESPONDING EX. OR COMP. EX. NO. | 3 SEM FIG. NO. | 14 REACTOR TEMP. (°C.) | 15 ON-STREAM TIME (MINS.) | 16 CONV. (%) | 17 $C_2^= + C_3^=$ SEL. (%) | 18 YIELD (%) |
|---|---|---|---|---|---|---|---|
| 1 | Ex. 1 | 1A,B | 335 | 7.0 | 100 | 15.0 | 15.0 |
| 2 | Ex. 1 | 1A,B | 335 | 29 | 100 | 16.0 | 16.0 |
| 3 | Ex. 1 | 1A,B | 335 | 92 | 100 | 19.0 | 19.0 |
| 4 | Ex. 1 | 1A,B | 335 | 108 | 96.4 | 27.7 | 26.7 |
| 5 | Ex. 1 | 1A,B | 335 | 113 | 92.0 | 28.0 | 25.8 |
| 6 | C. Ex. 1 | 2 | 335 | 7 | 88.0 | 25.0 | 22.0 |
| 7 | C. Ex. 1 | 2 | 335 | 22 | 58.0 | 48.0 | 27.8 |
| 8 | C. Ex. 2 | 3 | 335 | 2 | 97.0 | 25.0 | 24.2 |
| 9 | C. Ex. 2 | 3 | 335 | 9 | 69.0 | 34.0 | 23.5 |
| 10 | C. Ex. 2 | 3 | 335 | 11 | 61.0 | 38.0 | 23.2 |
| 11 | C. Ex. 2 | 3 | 335 | 19 | 10.0 | 63.0 | 6.3 |
| 12 | Ex. 2 | 1A,B | 335 | 20 | 100 | 28.0 | 28.0 |

TABLE 1-continued

| | | | | | | | |
|---|---|---|---|---|---|---|---|
| 13 | (M/T) Ex. 2 | 1A,B | 335 | 53 | 100 | 24.0 | 24.0 |
| 14 | (M/T) Ex. 2 | 1A,B | 335 | 80 | 100 | 25.0 | 25.0 |
| 15 | Ex. 2 (M/T) | 1A,B | 335 | 109 | 100 | 27.0 | 27.0 |
| 16 | Ex. 2 (M/T) | 1A,B | 335 | 111 | 92 | 28.0 | 25.8 |
| 17 | C. Ex. 3 | 3 | 335 | 2 | 91 | 31.0 | 28.2 |
| 18 | (M/T) C. Ex. 3 | 3 | 335 | 6 | 81 | 39.0 | 31.6 |
| 19 | (M/T) C. Ex. 3 | 3 | 335 | 11 | 60 | 40.0 | 24.0 |
| 20 | C. Ex. 4 | 4 | 335 | 40 | 86 | 40.0 | 34.4 |
| 21 | C. Ex. 4 | 4 | 335 | 55 | 58 | 44.0 | 25.5 |

*(S) = Stirred

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for converting a feed to a mixture rich in olefins which comprises contacting, under conversion conditions at a conversion reaction temperature of from about 250° to about 500° C., said feed comprising one or more monohydric alcohols having from about 1 to about 4 carbon atoms, ethers derived therefrom, or mixtures of said alcohols and ethers, with a crystalline aluminosilicate zeolite, said zeolite being prepared by the process comprising:
   (A) admixing to form a reaction mixture in the absence of a buffer:
      (a) at least one tetraalkyl ammonium hydroxide in an amount sufficient to impart a pH to the reaction mixture in the initial absence of said acid of (f) of not less than 13, when measured at room temperature;
      (b) at least one sodium cation source;
      (c) at least one silica source;
      (d) at least one alumina source;
      (e) water; and
      (f) at least one inorganic acid in a manner and under conditions sufficient to (i) impart a $SiO_2/Al_2O_3$ mole ratio of from about 70 to about 2000 to the crystalline zeolite; (ii) impart a $Na_2O/SiO_2$ mole ratio to said admixture of at least 0.05 and (iii) adjust, with said acid, the initial pH of the reaction mixture, when measured at room temperature, to be from about 11.3 to about 11.7;
   (B) heating the reaction mixture until crystals of said zeolite form;
   (C) separating said crystals from the reaction mixture; and
   (D) converting the resulting crystals to the hydrogen form by exchange and calcination.

2. The process of claim 1 wherein in said zeolite preparative procedure said tetraalkylammonium hydroxide is tetrapropylammonium hydroxide, the silica and sodium source is sodium silicate, the aluminum source is aluminum nitrate, and the acid is $HNO_3$.

3. The process of claim 1 wherein the feed comprises at least one monohydric alcohol and additionally comprises at least one aromatic compound.

4. The process of claim 3 wherein the feed further comprises steam.

5. A process for converting a feed to a mixture rich in olefins which comprises contacting, under conversion conditions at a conversion reaction temperature of from about 250° to about 500° C., said feed comprising one or more monohydric alcohols having from about 1 to about 4 carbon atoms, ethers derived therefrom, or mixtures of said alcohols and ethers, with a crystalline aluminosilicate ZSM-5 zeolite, said zeolite being prepared by the process comprising:
   (1) providing, in the absence of a buffer, a reaction mixture comprising tetrapropylammonium hydroxide, a silica source, an alumina source, a sodium cation source and water, said reaction mixture components being present in amounts sufficient to impart: (i) an initial pH to the reaction mixture of not less than about 13; and (ii) a composition to the reaction mixture expressed in terms of mole ratios comprising:

| | |
|---|---|
| $(TPA)_2O/SiO_2$ | 0.05 to 1 |
| $SiO_2/Al_2O_3$ | 220 to 800 |
| $H_2O/SiO_2$ | 20 to 140 |
| $OH^-/SiO_2$ | 0.2 to 5 |
| $H_2O/OH^-$ | 10 to 200 |
| $Na_2O/SiO_2$ | 0.1 to 4 | wherein TPA signifies tetrapropylamminium;
   (2) adjusting the pH of the reaction mixture to between about 11.4 and about 11.6 when measured at room temperature, by the addition of nitric acid;
   (3) heating the pH adjusted reaction mixture in a manner and under conditions sufficient to cause crystals of said zeolite to form;
   (4) separating said crystals from the reaction mixture; and
   (5) converting the resulting crystals to the hydrogen form by exchange and calcination.

6. The process of claim 5 wherein the feed comprises methanol.

7. The process of claim 5 wherein the feed comprises dimethylether.

8. The process of claim 7 wherein the feed contains steam in an amount sufficient to provide a mole ratio of dimethylether to steam therein of from about 1:5 to about 1:0.2.

9. The process of claim 6 wherein the feed additionally comprises at least one aromatic compound selected from the group consisting of benzene, toluene, and paraoxylene.

10. The process of claim 9 wherein said feed further comprises steam in an amount sufficient to achieve a methanol to water mole ratio to from about 1:0.05 to about 1:0.7.

* * * * *